United States Patent
Xu et al.

(10) Patent No.: US 9,155,475 B2
(45) Date of Patent: *Oct. 13, 2015

(54) ENABLING HYBRID VIDEO CAPTURE OF A SCENE ILLUMINATED WITH UNSTRUCTURED AND STRUCTURED ILLUMINATION SOURCES

(75) Inventors: Beilei Xu, Penfield, NY (US); Lalit Keshav Mestha, Fairport, NY (US); Edgar A. Bernal, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 60 days.

This patent is subject to a terminal disclaimer.

(21) Appl. No.: 13/533,605

(22) Filed: Jun. 26, 2012

(65) Prior Publication Data

US 2013/0342756 A1     Dec. 26, 2013

(51) Int. Cl.
| | |
|---|---|
| H04N 5/232 | (2006.01) |
| A61B 5/00 | (2006.01) |
| H04N 5/225 | (2006.01) |
| H04N 5/235 | (2006.01) |

(52) U.S. Cl.
CPC ............. *A61B 5/0077* (2013.01); *A61B 5/0073* (2013.01); *H04N 5/2256* (2013.01); *H04N 5/23296* (2013.01); *H04N 5/2354* (2013.01)

(58) Field of Classification Search
CPC H04N 5/2354; H04N 5/2256; H04N 5/23296
USPC .................................................. 348/370, 371
See application file for complete search history.

(56) References Cited

U.S. PATENT DOCUMENTS

| | | | | |
|---|---|---|---|---|
| 6,751,344 B1 * | 6/2004 | Grumbine | ..................... | 382/154 |
| 2002/0140670 A1 * | 10/2002 | Albeck et al. | ................. | 345/156 |
| 2002/0140821 A1 * | 10/2002 | Segev et al. | .............. | 348/207.99 |
| 2002/0181742 A1 * | 12/2002 | Wallace et al. | ................ | 382/104 |
| 2003/0098969 A1 * | 5/2003 | Katz et al. | ........................ | 356/73 |
| 2004/0008274 A1 * | 1/2004 | Ikari et al. | ...................... | 348/370 |
| 2004/0183940 A1 * | 9/2004 | Raskar | .......................... | 348/371 |
| 2004/0212725 A1 * | 10/2004 | Raskar | .......................... | 348/370 |
| 2006/0268153 A1 * | 11/2006 | Rice et al. | ..................... | 348/370 |
| 2007/0263903 A1 * | 11/2007 | St. Hilaire et al. | ............ | 382/106 |
| 2007/0268398 A1 * | 11/2007 | Raskar et al. | ................. | 348/370 |

(Continued)

OTHER PUBLICATIONS

Mestha et al., "3D Imaging Using Structured Light for Accurate Vehicle Occupancy Determination", U.S. Appl. No. 13/476,334, filed May 21, 2012.

(Continued)

*Primary Examiner* — Nicholas Giles
*Assistant Examiner* — Abdelaaziz Tissire
(74) *Attorney, Agent, or Firm* — Philip E. Blair; Fleit Gibbons Gutman Bongini & Bianco P.L.

(57) ABSTRACT

What is disclosed is a system and method for enabling hybrid video capture of a scene being illuminated with structured and unstructured illumination sources over a wavelength range of interest that significantly intersects with each other. In one embodiment, the present system comprises a video capture device for capturing video of a scene being actively illuminated by both a structured and unstructured illumination source; a controller for controlling a manipulation of at least one structured and at least one unstructured illumination sources during capture of the video by the video capture device; and a processor in communication with the controller, the processor executing machine readable program instructions effectuating the manipulation. Various embodiments are disclosed.

15 Claims, 5 Drawing Sheets

(56) References Cited

U.S. PATENT DOCUMENTS

| | | | |
|---|---|---|---|
| 2008/0204704 A1* | 8/2008 | Rankin et al. | 356/28 |
| 2008/0277473 A1* | 11/2008 | Kotlarsky et al. | 235/462.07 |
| 2009/0115779 A1* | 5/2009 | Shulman et al. | 345/419 |
| 2010/0066824 A1* | 3/2010 | Burton | 348/89 |
| 2010/0165179 A1* | 7/2010 | Kawamura | 348/371 |
| 2010/0238344 A1* | 9/2010 | Tsai | 348/361 |
| 2010/0317398 A1* | 12/2010 | Thorn | 455/556.1 |
| 2011/0052082 A1* | 3/2011 | Parkov et al. | 382/209 |
| 2011/0117532 A1* | 5/2011 | Relyea et al. | 434/307 R |
| 2013/0324830 A1* | 12/2013 | Bernal et al. | 600/407 |
| 2013/0324874 A1* | 12/2013 | Bernal et al. | 600/534 |
| 2013/0324875 A1* | 12/2013 | Mestha et al. | 600/534 |
| 2013/0324876 A1* | 12/2013 | Bernal et al. | 600/538 |
| 2013/0343634 A1* | 12/2013 | Xu et al. | 382/154 |

OTHER PUBLICATIONS

Wang et al., "Multi-Band Infrared Camera System Optimized for Skin Detection", U.S. Appl. No. 13/416,436, filed Mar. 9, 2012.

Mestha et al., "Filtering Source Video Data Via Independent Component Selection", U.S. Appl. No. 13/281,975, filed Oct. 26, 2011.

Mestha et al., "Removing Environment Factors From Signals Generated From Video Images Captured for Biomedical Measurements", U.S. Appl. No. 13/401,207, filed Feb. 21, 2012.

Jean-Francois Cardoso, "Blind signal separation: statistical principles", pp. 1-16, (Official Version published as: Proceedings of the IEEE, vol. 9, No. 10, pp. 2009-2025, Oct. 1998).

Hyvarinen, et al., "Independent Component Analysis: Algorithms and Applications", Neural Networks Research Centre, Helsinki University of Technology, Finland, Neutral Networks, pp. 1-31, 13(4-5); 411-430, 2000.

Jason Geng, "Structured-Light 3D Surface Imaging: A Tutorial", Advances in Optics and Photonics vol. 3, pp. 128-160, Optical Society of America, Mar. 31, 2011.

Xu et al., "Contemporaneously Reconstructing Images Captured of a Scene Illuminated With Unstructured and Structured Illumination Sources", U.S. Appl. No. 13/533,678, filed Jun. 26, 2012.

\* cited by examiner

ENABLING HYBRID VIDEO CAPTURE OF A SCENE ILLUMINATED WITH UNSTRUCTURED AND STRUCTURED ILLUMINATION SOURCES

CROSS REFERENCE TO RELATED APPLICATIONS

The present patent application is related to commonly owned and concurrently filed U.S. patent application Ser. No. 13/533,678 entitled: "Contemporaneously Reconstructing Images Captured Of A Scene Illuminated With Unstructured And Structured Illumination Sources", by Xu et al., which is incorporated herein in its entirety by reference.

TECHNICAL FIELD

The present invention is directed to systems and methods for enabling the capture of video of a scene illuminated with unstructured and structured illumination sources.

BACKGROUND

Monitoring cardiac and respiratory events is of clinical importance in the early detection of potentially fatal conditions. Current technologies involve contact sensors the individual must wear constantly. Such a requirement can lead to patient discomfort, dependency, loss of dignity, and further may fail due to a variety of reasons including refusal to wear the monitoring device. Elderly patients are even more likely to suffer from the adverse effects of continued monitoring. Unobtrusive, non-contact, imaging based methods are increasingly needed for monitoring patients. One such system uses a single channel camera under structured and unstructured illuminations to capture video of a subject of interest such that the system can monitor both the cardiac and respiratory events. The system isolates pixels associated with the subject's vascular pathways within each frame from the image frames comprising pixels with intensity values corresponding to detected reflected energy projected by unstructured illumination source and estimates subject's chest volume by reconstructing 3D depth map from the image frames comprising pixels corresponding to detected reflected energy projected by structured illumination source. This system requires the simultaneous projection of structured and unstructured light sources. However, artifacts due to the interference caused by the use of structured light patterns have arisen. Such artifacts can adversely impact on the 3D surface reconstruction and vascular pattern detection. For example, FIG. 1 shows an image of a random structured light pattern projected onto a subject's hand. FIG. 2 shows pixels having been classified as corresponding to the projected structured illumination pattern in the image of FIG. 1. Pixels from the projected dot pattern of the structured illumination source can alter the extracted underlying vascular patterns even when interpolated with values of surrounding pixels, especially wherein the blood vessels therein are narrow or short and the projected dot pattern has a relatively high density. This can negatively impact cardiac/respiratory data derived from information associated with pixels of the subject's blood vessels.

Accordingly, what is needed in this art are sophisticated methods for enabling hybrid video capture of a scene being illuminated with structured and unstructured illumination sources.

INCORPORATED REFERENCES

The following U.S. patents, U.S. patent applications, and Publications are incorporated herein in their entirety by reference.

"3D Imaging Using Structured Light For Accurate Vehicle Occupancy Determination", U.S. patent application Ser. No. 13/476,334, by Mestha et al.

"Processing A Video For Vascular Pattern Detection And Cardiac Function Analysis", U.S. patent application Ser. No. 13/483,992, by Mestha et al.

"Filtering Source Video Data Via Independent Component Selection", U.S. patent application Ser. No. 13/281,975, by Mestha et al.

"Removing Environment Factors From Signals Generated From Video Images Captured For Biomedical Measurements", U.S. patent application Ser. No. 13/401,207, by Mestha et al.

"*Blind Signal Separation: Statistical Principles*", Jean-Francois Cardoso, Proceedings of the IEEE, Vol. 9, No. 10, pp. 2009-2025, (October 1998).

"*Independent Component Analysis: Algorithms And Applications*", Aapo Hyvärinen and Erkki Oja, Neural Networks, 13(4-5), pp. 411-430, (2000).

"*Structured-Light 3D Surface Imaging: A Tutorial*", by Jason Geng, Advances in Optics and Photonics Vol. 3, pp. 128-160, (Mar. 31, 2011) Optical Society of America.

BRIEF SUMMARY

What is disclosed is a system for enabling hybrid video capture of a scene being illuminated with structured and unstructured illumination sources. In one embodiment, the present system comprises a video capture device for capturing video of a scene being actively illuminated by both a structured and unstructured illumination source; a controller for controlling a manipulation of at least one of the structured and unstructured illumination sources during capture of the video by the video capture device; and a processor in communication with the controller, the processor executing machine readable program instructions effectuating the manipulation. Various embodiments are disclosed.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

Figure 1:
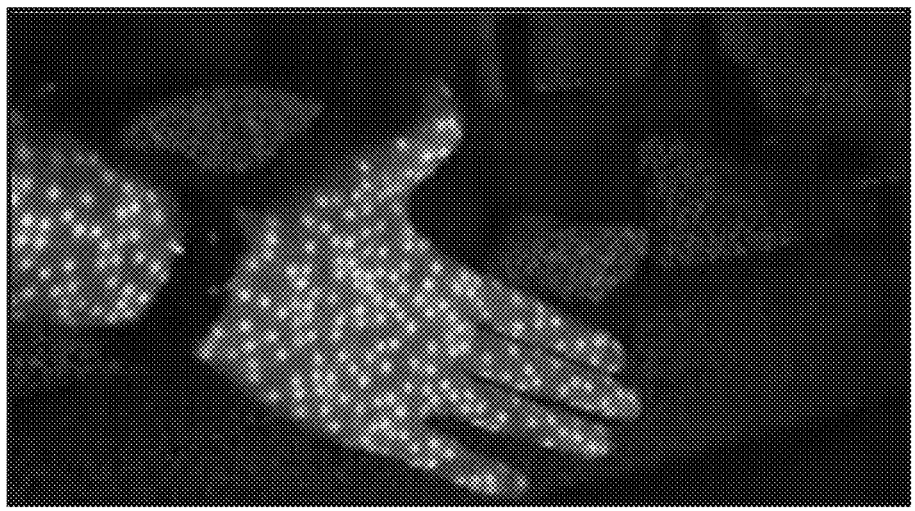
FIG. 1 shows an image of a projected random structured light pattern onto a subject's hand.
Figure 2:
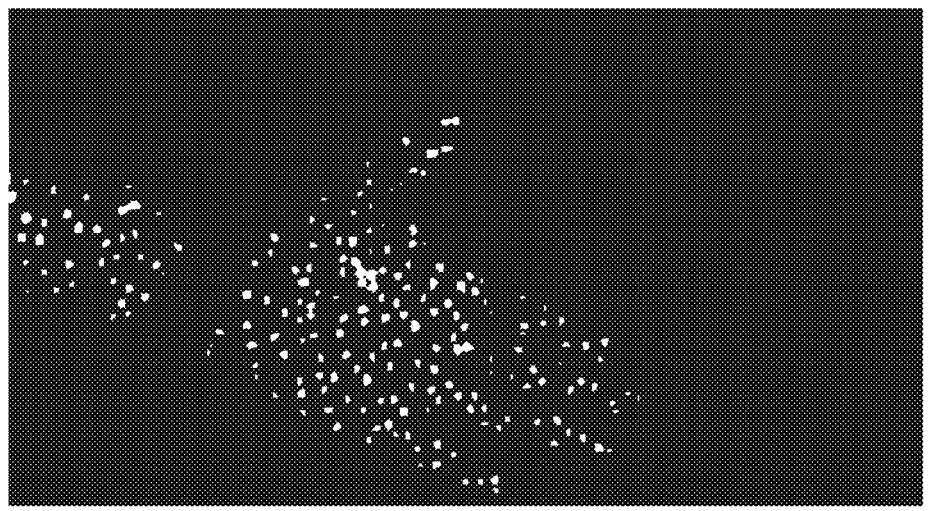
FIG. 2 shows pixels classified as corresponding to the projected structured illumination pattern in the image of FIG. 1.

What is disclosed is a system for enabling hybrid video capture of a scene being illuminated with structured and unstructured illumination sources.

Non-Limiting Definitions

A "region of interest" refers to one or more regions or areas of a subject of interest being video-taped using a video capture device. What defines a region of interest will largely depend on the application wherein the teachings hereof find their intended uses. For example, if the video is being captured of a subject to facilitate a determination of cardiorespiratory function then the region of interest would be an area of the subject's exposed skin such as, for instance, face, chest, neck, etc. A region of interest may be the entire image.

A "video capture device" is a device for acquiring a video. In one embodiment, the video capture device is a single channel device operating in a wavelength of interest such as visible or near infrared. In another embodiment, a multi-channel device operating in overlapping wavelength bands.

A "video", as is generally understood, is a plurality of 2D image frames captured over time. The video may also contain other components such as, audio, time reference signals, and the like.

"Unstructured illumination" refers to ambient light or an external light source such as a light bulb.

"Structured illumination" is an illumination source which projects light through a patterned grid or window.

"Manipulating the illumination sources", as used herein, refers to spatially, temporally, and/or spectrally varying the structured and unstructured illumination sources during capture of the video by the video capture device. In one embodiment where the unstructured illumination source is an ambient light source, the manipulating comprises sequentially alternating a projection of the structured illumination source onto the scene during video capture; selectively choosing a region of interest in the scene with the region being illuminated by the structured illumination source and by ambient light, while the rest of the scene is illuminated by ambient light alone; or spectrally multiplexing the structured illumination source by making its wavelength range narrower than the wavelength range of ambient light such that reflected energy from both sources can be recovered via filtering. In another embodiment where the unstructured illumination source is not an ambient light source, the manipulating comprises any of the following: sequentially alternating a projection of the structured and unstructured illumination sources such that neither of the sources is projecting light concurrently; selectively choosing a first and second region of interest in the scene, the first region being illuminated by the structured illumination source and the second region being illuminated by the unstructured illumination source, such that neither of the sources is concurrently projecting light onto a same region; and spectrally multiplexing the illumination sources by making the wavelength range of a first of the illumination sources narrower than a wavelength range of a second of the illumination sources such that reflected energy from both sources can be recovered via filtering. An illumination source can be varied spatially by, for instance, a device controller moving that illumination source such that the source light is projected onto certain regions in the scene from different angles. An illumination source can be varied temporally by, for instance, a device controller toggling the projection of the source light on/off according to a schedule or a desired periodicity. An illumination source can be varied spectrally by, for instance, a device controller selecting a narrow and a broad wavelength bands for the structured and unstructured illumination. A controller can be configured to vary the intensity of the source light that an illumination source projects.

A "2D intensity pixel map" is a map of a region of interest composed of pixel intensity values obtained by the spectral sensor of the video capture device. In one embodiment, the 2D intensity pixel map is a map of the subject's vascular pattern containing blood vessels which transport hemoglobin.

Figure 3:
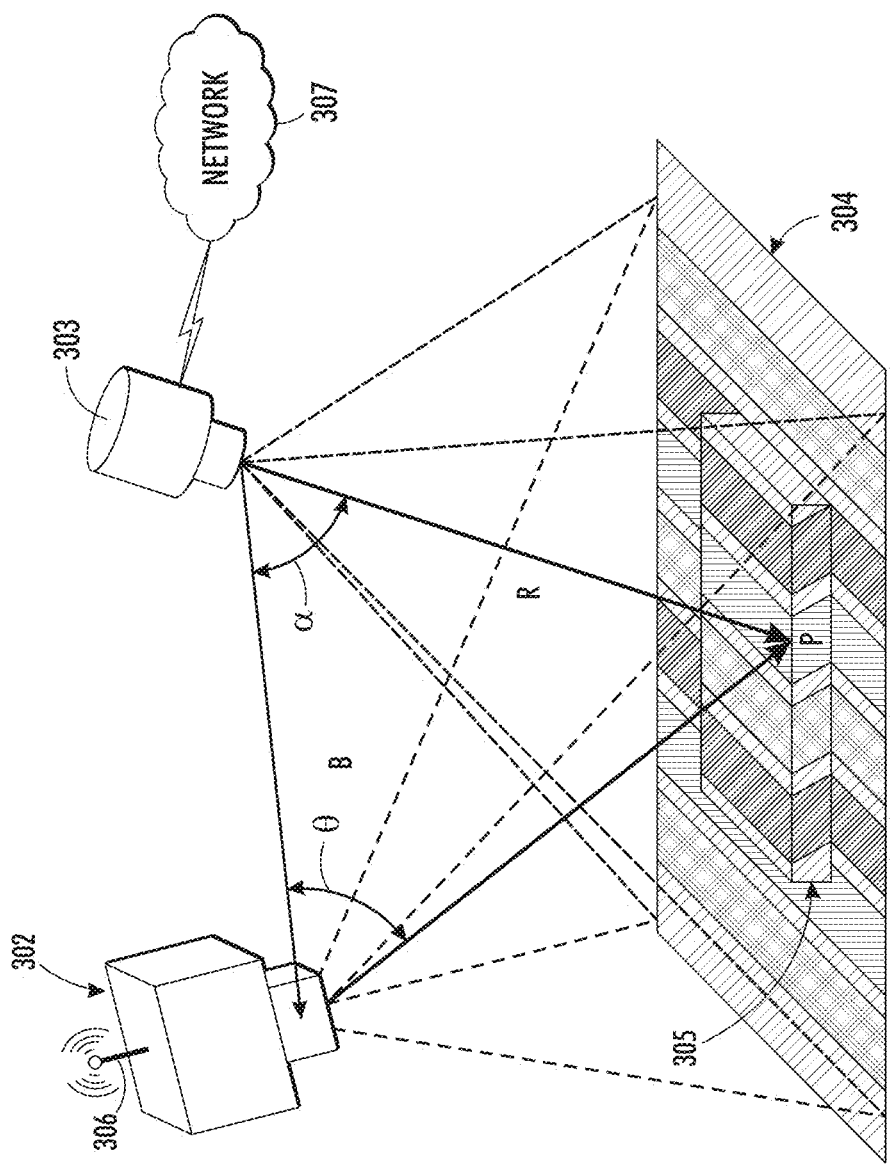
FIG. 3 shows a structured illumination source and a video camera 303 for capturing a 2D image of scene containing 3D object.

A "3D surface map" is a map of a surface of a region of interest that is reconstructed using a 3D imaging technique which extracts depth information for pixel locations throughout the region based upon the amount of distortion of a structured light pattern reflected from surfaces in that region of the image. When the surface in a scene is non-planar and contains a 3D object, the geometric shape of the surface distorts the projected structured light pattern. Such distortions are detected by the imaging device enabling the accurate reconstruction of 3D surface maps using various principles and algorithms that are well established. As shown by way of example in FIG. 3, hybrid video capture device 303 acquires a video of scene 304 containing example 3D object 305 being illuminated by a structured illumination source 302 shown having a communication element 306 to effectuate a bi-directional communication with a remote device, such as a computer workstation or device controller. Hybrid video capture device 303 is in communication with one or more devices over network 307. A geometric relationship between device 303, structured illumination source 302, and an object surface point P is used to reconstruct the 3D surface map using a relationship expressed by a triangulation given by:

$$R = B\frac{\sin(\theta)}{\sin(\alpha + \theta)} \quad (1)$$

Example Dual Illumination Source Configuration

Figure 4:
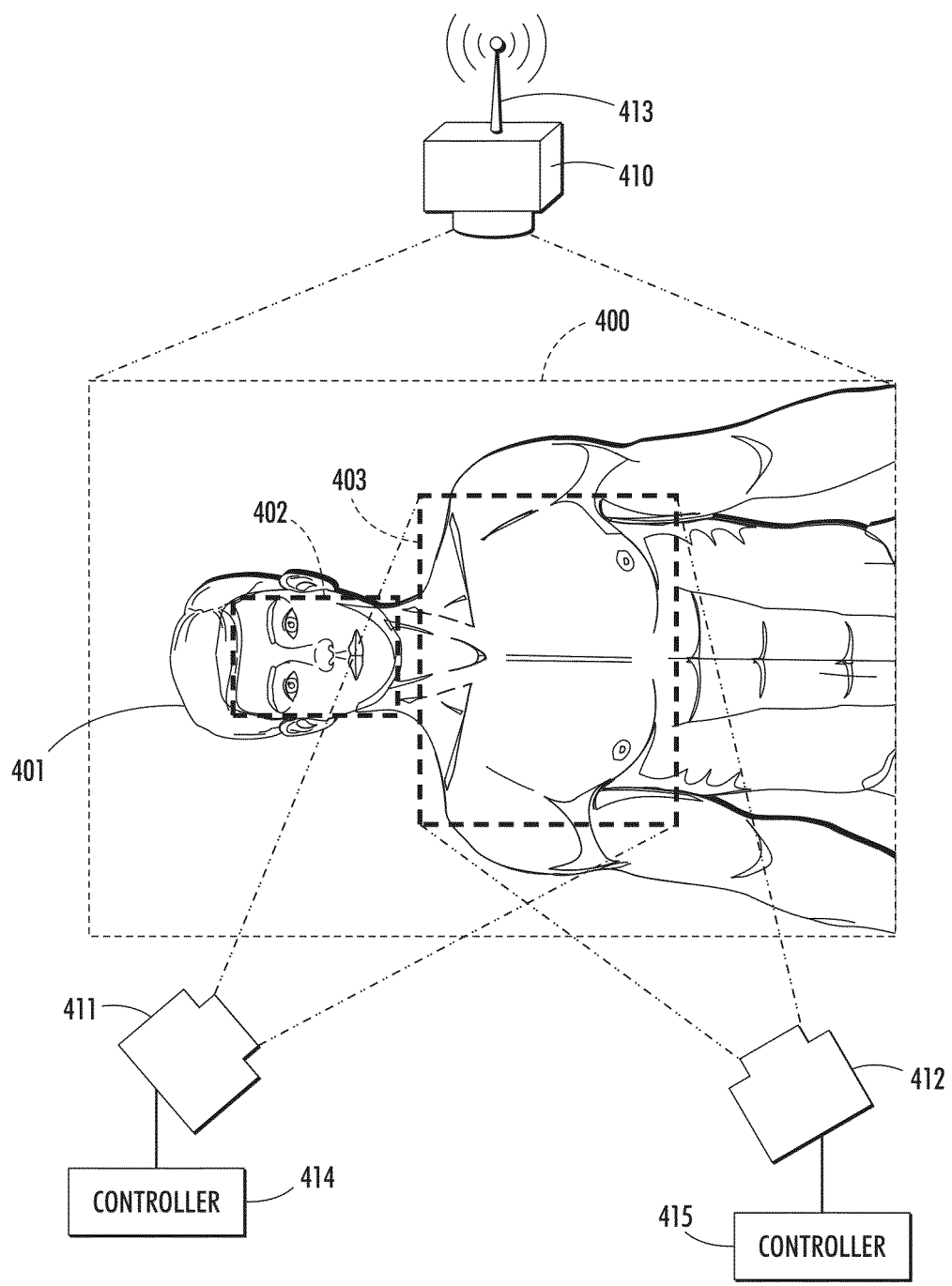
FIG. 4 illustrates an example scene illuminated with structured and unstructured light sources and a hybrid video capture device actively acquiring a video of a region of interest of a subject.

Reference is now being made to FIG. 4 which illustrates an example scene illuminated with structured and unstructured light sources and a video capture device actively acquiring a video of a region of interest of a subject. The regions of interest 402 and 403 in the scene 400 (e.g., face and chest) can be identified by processing the video using, for example, any of a variety of techniques including object identification, pixel classification, material analysis, texture identification, and/or pattern recognition. In one embodiment, hybrid video capture device 410, illustrated by way of example, captures reflected energy off chest 403 emitted by structured illumination source 411 and unstructured illumination source 412. Both illumination sources 411 and 412 can be manipulated such that their respective light sources can be spectrally and/or temporally varied in accordance with the teachings hereof. On another embodiment, hybrid video capture device 410, captures reflected energy off the face area 402 emitted by unstructured illumination source 412 and captures reflected energy off the chest area 403 emitted by structured illumination 411 such that their respective light source can be spatially separated in accordance with the teachings hereof. Hybrid device 410 is shown having a communication element 413 to effectuate a bi-directional communication with a remote device, such as a computer workstation or device controller. Controller 414 effectuates a manipulation of structured illumination source 411 in accordance herewith, and controller 415 effectuates a manipulation of unstructured illumination source 412 in accordance herewith. Controllers 414 and 415 are in communication via pathways not shown with various components of the special purpose computer of FIG. 6.

Flow Diagram of One Embodiment

Figure 5:
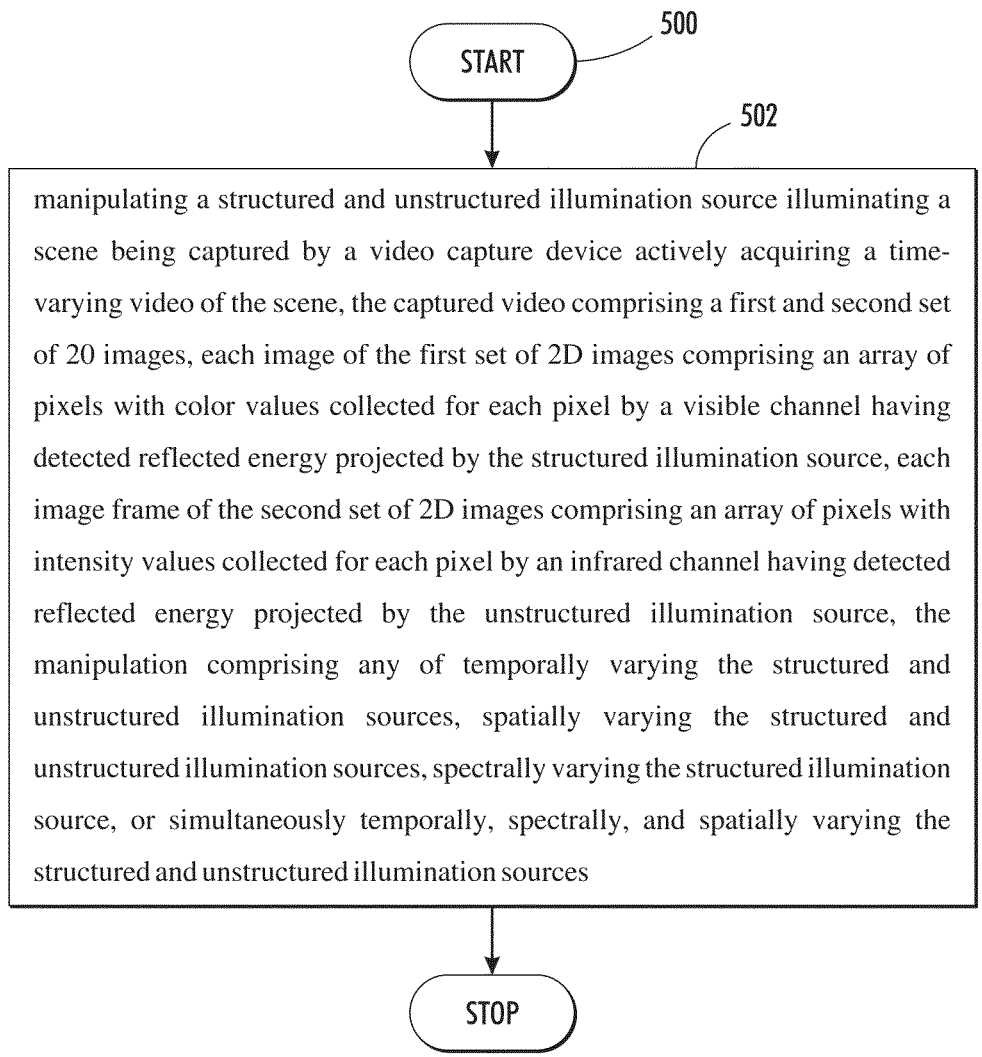
FIG. 5 is a flow diagram which illustrates one example embodiment of the present method for enabling hybrid video capture of a scene being illuminated with unstructured and structured illumination sources.

Reference is now being made to the flow diagram of FIG. 5 which illustrates one example embodiment of the present method for enabling hybrid video capture of a scene being illuminated with unstructured and structured illumination sources. Flow processing begins at step 500 and immediately proceeds to step 502.

At step 502, manipulating a structured and unstructured illumination source illuminating a scene being captured by a video capture device actively acquiring a video of the scene. The captured video comprises a first and second set of 2D images. Each image frame of the first set of 2D images comprises an array of pixels with values collected for each pixel by having detected reflected energy projected by the structured illumination source. Each image frame of the second set of 2D images comprises an array of pixels with intensity values collected for each pixel having detected reflected energy projected by the unstructured illumination source. The structured and unstructured illumination sources have significant overlapping spectral band that can be visible, infrared, or a wavelength band that covers both visible and infrared. In the embodiment where the unstructured illumination source is an ambient light source, the manipulating comprises: sequentially alternating a projection of the structured illumination source onto the scene during video capture; selectively choosing a region of interest in the scene with the region being illuminated by the structured illumination source and by ambient light, while the rest of the scene is illuminated by ambient light alone; or spectrally multiplexing the structured illumination source by making its wavelength range narrower than the wavelength range of ambient light such that reflected energy from both sources can be recovered via filtering. In the embodiment where the unstructured illumination source is not an ambient light source, the manipulating comprises: sequentially alternating a projection of the structured and unstructured illumination sources such that neither of the sources is projecting light concurrently; selectively choosing a first and second region of interest in the scene with the first region being illuminated by the structured illumination source and the second region being illuminated by the unstructured illumination source such that neither of the sources is concurrently projecting light onto a same region; or spectrally multiplexing the illumination sources by making the wavelength range of a first of the illumination sources narrower than a wavelength range of a second of the illumination sources such that reflected energy from both sources can be recovered via filtering. The alternating sequence can be determined by external events such as, for instance, a state change exceeding a pre-determined threshold, or a motion exceeding a pre-determined threshold, or be determined in accordance to a pre-selected sequence. The selectively choosing a first and second region of interest in the scene is depend on the types of signals that can be extracted from each region. For example, facial region (402) in FIG. 4 can be used to extract heart rate signals while monitoring the chest area (403) in FIG. 4 can be used to extract respiratory signals. The spectrally multiplexing is determined by the spectral characteristics of the desired signals. Thereafter, in this embodiment, further processing stops.

Example System for Manipulating Illumination Sources

Figure 6:
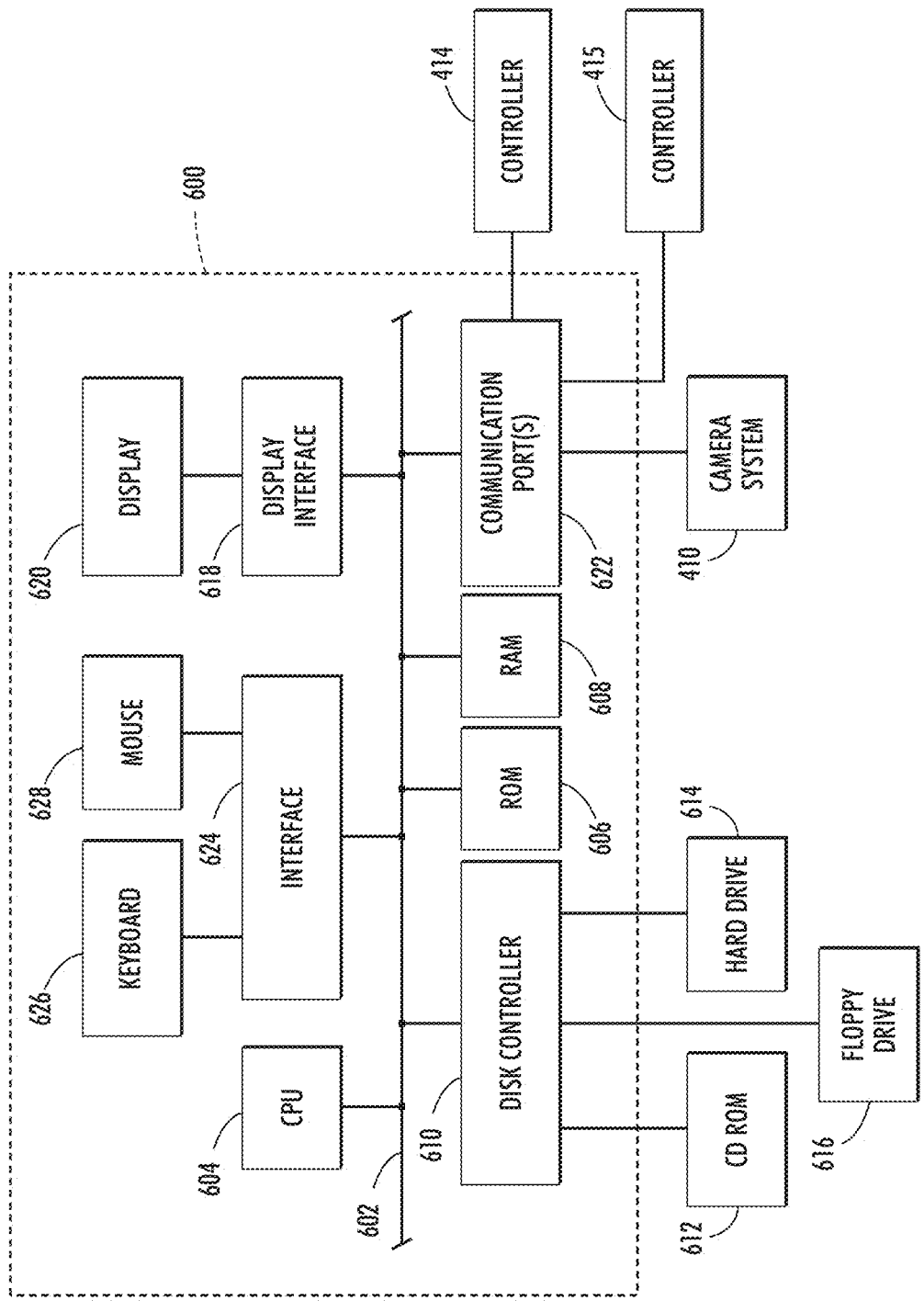
FIG. 6 illustrates a block diagram of one example special purpose computer for implementing various aspects of the present method as described with respect to the flow diagram of FIG. 5.

Reference is now being made to FIG. 6 which illustrates a block diagram of one example special purpose computer for implementing various aspects of the present method as described with respect to the flow diagram of FIG. 5. Such a special purpose processor is capable of executing machine executable program instructions for causing the controllers, 414 and 415, of FIG. 4 to manipulate the structured and unstructured illumination sources in accordance with the teachings hereof, and may comprise any of a micro-processor, micro-controller, ASIC, electronic circuit, or any combination thereof.

In FIG. 6, communications bus 602 is in communication with a central processing unit (CPU) 604 capable of executing machine readable program instructions for performing any of the calculations, comparisons, logical operations, and other program instructions for performing any of the steps described above with respect to the flow diagrams and illustrated embodiments hereof. Processor 604 is in communication with memory (ROM) 606 and memory (RAM) 608 which, collectively, constitute example storage devices. Such memory may be used to store machine readable program instructions and other program data and results to sufficient to carry out any of the functionality described herein. Disk controller 610 interfaces with one or more storage devices 614 which may comprise external memory, zip drives, flash memory, USB drives, or other devices such as CD-ROM drive 612 and floppy drive 616. Storage device stores machine executable program instructions for executing the methods hereof. Such storage devices may be used to implement a database wherein various records are stored. Display interface 618 effectuates the display of information on display 620 in various formats such as, for instance, audio, graphic, text, and the like. Interface 624 effectuates a communication via keyboard 626 and mouse 628, collectively a graphical user interface. Such a graphical user interface is useful for a user to enter information about any of the displayed information in accordance with various embodiments hereof. Communication with external devices may occur using example communication port(s) 622. Shown is communication port(s) 622 being placed in communication with the hybrid camera system 413 of FIG. 4 and each of the controllers 414 and 415 to effectuate a manipulation of the illumination sources 411 and 412. Such ports may be placed in communication with such devices over networks not shown such as, for example, the Internet or an intranet, either by wired or wireless links. Example communication ports include modems, network cards such as an Ethernet card, routers, a PCMCIA slot and card, USB ports, and the like, capable of transferring data from one device to another. Software and data is transferred via the communication ports in the form of signals which may be any of digital, analog, electromagnetic, optical, infrared, or other signals capable of being transmitted and/or received by the communications interface. Such signals may be implemented using, for example, a wire, cable, fiber optic, phone line, cellular link, RF, or other signal transmission means presently known in the arts or which have been subsequently developed.

The teachings hereof can be implemented in hardware or software using any known or later developed systems, structures, devices, and/or software by those skilled in the applicable art without undue experimentation from the functional description provided herein with a general knowledge of the relevant arts. The teachings hereof may be partially or fully implemented in software using object or object-oriented software development environments that provide portable source code that can be used on a variety of computer, workstation, server, network, or other hardware platforms. One or more of the capabilities hereof can be emulated in a virtual environment as provided by an operating system, specialized programs or leverage off-the-shelf computer graphics software such as that in Windows, Java, or from a server or hardware accelerator or other image processing devices.

One or more aspects of the methods described herein are intended to be incorporated in an article of manufacture, including one or more computer program products, having computer usable or machine readable media. The article of manufacture may be included on at least one storage device readable by a machine architecture embodying executable program instructions capable of performing the methodologies described herein. The article of manufacture may be included as part of a computer system, an operating system, a plug-in, or may be shipped, sold, leased, or otherwise provided separately either alone or as part of an add-on, update, upgrade, or product suite.

It will be appreciated that various of the above-disclosed and other features and functions, or alternatives thereof, may be combined into other systems or applications. Various presently unforeseen or unanticipated alternatives, modifications, variations, or improvements therein may become apparent and/or subsequently made by those skilled in the art which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for enabling hybrid video capture of a subject's exposed skin being illuminated with unstructured and structured illumination sources, the method comprising:
    manipulating at least one structured illumination source with light projected through a patterned grid and at least one unstructured illumination source illuminating a subject's exposed skin being captured by a video capture device actively acquiring a video of said subject's exposed skin, said video comprising a first and second set of 2D images, wherein said two sets of images may share a subset of common images, each image frame of said first set of 2D images comprising an array of pixels with pixel values corresponding to detected reflected energy projected by said structured illumination source, each image frame of said second set of 2D images comprising an array of pixels with intensity values defining a map of said subject's vascular pattern containing blood vessels which transport hemoglobin and corresponding to detected reflected energy projected by said unstructured illumination source wherein said unstructured illumination source is an ambient light source and said manipulating includes spectrally multiplexing said illumination sources by making a wavelength range of said structured illumination sources narrower than a wavelength range of said unstructured illumination source such that reflected energy from both illumination sources can be recovered via filtering, said unstructured and structured illumination sources having overlapping spectral bands.

2. The method of claim 1, wherein said manipulating includes sequentially alternating a projection of said structured and unstructured illumination sources such that neither of said illumination sources is projecting light concurrently and said alternating sequence is determined by one of: external events and a pre-selected sequence.

3. The method of claim 2, wherein said external events include any of: a state change exceeding a pre-determined threshold, and a motion exceeding a pre-determined threshold.

4. The method of claim 1, wherein said structured and unstructured illumination sources comprise one of: visible, infrared and a combination of visible and infrared.

5. The method of claim 1, further comprising identifying at least one region of interest in said subject's exposed skin using any of: object identification, pixel classification, material analysis, texture identification, and pattern recognition.

6. A system for enabling hybrid video capture of a subject's exposed skin being illuminated with unstructured and structured illumination sources, the system comprising:
    a video capture device for capturing video of a subject's exposed skin being actively illuminated by both a structured illumination source with light projected through a patterned grid and unstructured illumination source, said unstructured illumination source is an ambient light source, said unstructured and structured illumination sources having overlapping spectral bands and said video comprising a first and second set of 2D images, wherein said two sets of images may share a subset of common images, each image frame of said first set of 2D images comprising an array of pixels with pixel values corresponding to detected reflected energy projected by said structured illumination source, each image frame of said second set of 2D images comprising an array of pixels with intensity values defining a map of said subject's vascular pattern containing blood vessels which transport hemoglobin;
    a controller for controlling a manipulation of at least one of said structured and unstructured illumination sources during capture of said video by said video capture device, and said manipulating includes spectrally multiplexing said illumination sources by making a wavelength range of said structured illumination sources narrower than a wavelength range of said unstructured illumination source such that reflected energy from both illumination sources can be recovered via filtering; and
    a processor in communication with said controller, said processor executing machine readable program instructions effectuating said manipulation.

7. The system of claim 6, wherein said unstructured illumination source is an ambient light source, said manipulating comprising sequentially alternating a projection of said structured illumination source onto said subject's exposed skin during video capture.

8. The system of claim 6, wherein said manipulating includes sequentially alternating a projection of said structured and unstructured illumination sources such that neither of said illumination sources is projecting light concurrently and said alternating sequence is determined by one of: external events and a pre-selected sequence.

9. The system of claim 8, wherein said external events include any of: a state change exceeding a pre-determined threshold, and a motion exceeding a pre-determined threshold.

10. The system of claim 6, wherein said structured and unstructured illumination sources comprise one of: visible, infrared and a combination of visible and infrared.

11. A computer implemented method for enabling hybrid video capture of a subject's exposed skin being illuminated with unstructured and structured illumination sources, the method comprising:

manipulating at least one structured illumination source with light projected through a patterned grid and at least one unstructured illumination source illuminating a subject's exposed skin being captured by a video capture device actively acquiring a video of said subject's exposed skin, said video comprising a first and second set of 2D images, wherein said two sets of images may share a subset of common images, each image frame of said first set of 2D images comprising an array of pixels with pixel values corresponding to detected reflected energy projected by said structured illumination source, each image frame of said second set of 2D images comprising an array of pixels with intensity values defining a map of said subject's vascular pattern containing blood vessels which transport hemoglobin and corresponding to detected reflected energy projected by said unstructured illumination source wherein said unstructured illumination source is an ambient light source and said manipulating includes spectrally multiplexing said illumination sources by making a wavelength range of said structured illumination sources narrower than a wavelength range of said unstructured illumination source such that reflected energy from both illumination sources can be recovered via filtering, said unstructured and structured illumination sources having overlapping spectral bands.

12. The computer implemented method of claim 11 wherein manipulating includes sequentially alternating a projection of said structured and unstructured illumination sources such that neither of said illumination sources is projecting light concurrently and said wherein said alternating sequence is determined by one of: external events and a pre-selected sequence.

13. The computer implemented method of claim 12, wherein said external events include any of: a state change exceeding a pre-determined threshold, and a motion exceeding a pre-determined threshold.

14. The computer implemented method of claim 12, wherein said structured and unstructured illumination sources comprise one of: visible, infrared and a combination of visible and infrared.

15. The computer implemented method of claim 12, further comprising identifying at least one region of interest in said subject's exposed skin using any of: object identification, pixel classification, material analysis, texture identification, and pattern recognition.

* * * * *